US005174296A

United States Patent [19]

Watanabe et al.

[11] Patent Number: 5,174,296

[45] Date of Patent: Dec. 29, 1992

[54] ULTRASONIC PROBE HAVING A PIEZOELECTRICAL ELEMENT

[75] Inventors: Kazuhiro Watanabe, Tokyo; Kenichi Hayakawa, Kawasaki; Hiroshi Ishikawa, Yokohama; Yasushi Hara; Kiyoto Matsui, both of Kawasaki; Kenji Kawabe, Yokohama; Takaki Shimura, Machida, all of Japan

[73] Assignee: Fujitsu Limited, Kanagawa, Japan

[21] Appl. No.: 676,481

[22] Filed: Mar. 28, 1991

[30] Foreign Application Priority Data

Mar. 29, 1990 [JP] Japan .................................. 2-81812

[51] Int. Cl.[5] ................................................ A61B 8/00

[52] U.S. Cl. .......................... 128/662.06; 128/660.09; 128/662.03

[58] Field of Search ...................... 128/662.06, 660.09, 128/660.10, 662.03; 606/7, 1

[56] References Cited

U.S. PATENT DOCUMENTS

| | | | |
|---|---|---|---|
| 3,955,561 | 5/1976 | Eggleton | 128/660.10 |
| 4,524,623 | 6/1983 | Terwilliger | 73/633 |
| 4,576,177 | 3/1986 | Webster, Jr. | 606/7 |
| 4,858,613 | 8/1989 | Fry et al. | 128/660.09 |
| 4,888,861 | 12/1989 | Day | 29/25.35 |
| 4,993,416 | 2/1991 | Ophir | 128/660.09 |
| 5,022,399 | 6/1991 | Biegeleisen | 128/662.06 |

FOREIGN PATENT DOCUMENTS

| | | |
|---|---|---|
| 79284A1 | 11/1982 | European Pat. Off. . |
| 308644A2 | 8/1988 | European Pat. Off. . |
| 310380A2 | 9/1988 | European Pat. Off. . |
| 3365482A1 | 10/1987 | Fed. Rep. of Germany . |

OTHER PUBLICATIONS

IEEE 1989 Ultrasonics Symposium, Proceedings 3–6 Oct. 1989. Montreal, Quebec, vol. 2, Editor B. R. McAvoy, pp. 695–698, IEEE; A. Cochran et al.: "Beam Forming in Solids Using Monolithic Ultrasonic Arrays".

International Publication No. WO 83/00009, International Publication date: Jan. 6, 1983. International Patent Classification A61B 10/00.

*Primary Examiner*—Kyle L. Howell

*Assistant Examiner*—George Manuel

*Attorney, Agent, or Firm*—Nikaido, Marmelstein, Murray & Oram

[57] ABSTRACT

An ultrasonic probe includes a housing, and a plurality of piezoelectric elements radially arranged in a plane substantially perpendicular to a direction in which the ultrasonic probe is inserted into a hollow portion to be scanned. The ultrasonic probe also includes an electrical part for carrying electricity to the piezoelectric elements to thereby cause the piezoelectric elements to emit ultrasonic waves and for carrying, to an external device, electric signals generated from the ultrasonic waves reflected by the hollow portion and received by the piezoelectric elements.

24 Claims, 15 Drawing Sheets

ULTRASONIC PROBE HAVING A PIEZOELECTRICAL ELEMENT

BACKGROUND OF THE INVENTION

The present invention generally relates to an ultrasonic probe which projects an ultrasonic wave onto a living human body and receives a wave reflected in the body, so that information related to the body can be obtained from the reflected wave. More particularly, the present invention is concerned with an ultrasonic probe having a piezoelectric element.

Recently, a diagnostic method using an ultrasonic probe has been to be practically used. An ultrasonic probe is inserted into a part of a living human body, for example, a blood vessel, and the inside thereof is scanned by an ultrasonic wave emitted from the ultrasonic probe.

FIG. 1A illustrates a first conventional ultrasonic probe, which has a piezoelectric element 102 supported by a rotating shaft 101. An ultrasonic wave emitted from the piezoelectric element 102 is deflected in a plane substantially perpendicular to a direction in which the ultrasonic probe is inserted into the human body.

FIG. 1B illustrates a second conventional ultrasonic probe, which has a reflection plate 104 supported by the rotating shaft 101. The piezoelectric element 102 is held stationary in the probe. The ultrasonic wave is deflected in the same way as that shown in FIG. 1A.

FIG. 1C illustrates a third conventional ultrasonic probe, which has a plurality of piezoelectric elements 105 arranged on a circumferential surface of a cylinder 103. The ultrasonic probe shown in FIG. 1C scans a plane substantially perpendicular to the direction in which it is inserted into the human body.

The first through third conventional ultrasonic probes, shown, respectively, in FIGS. 1A through 1C, do not have a visual field in front of the probe, that is, in the direction in which the probe is inserted into the human body. There is a need to emit the ultrasonic wave in the probe inserting direction and obtain information about the area in front of the probe. FIG. 2 shows such an ultrasonic probe. An ultrasonic probe 108 is inserted into a blood vessel 107 of a human body, and forwardly emits an ultrasonic wave. Then, the ultrasonic probe 108 receives a reflected ultrasonic wave, which has information about the area in front of the probe 108.

Normally, a blood vessel of a living human body has a diameter of approximately 3–10 mm. Some ultrasonic probes capable of forwardly emitting ultrasonic waves are known. However, such conventional ultrasonic probes cannot be produced in a size compact enough to be inserted into such blood vessels of living human bodies.

SUMMARY OF THE INVENTION

It is a general object of the present invention to provide a novel and useful ultrasonic probe in which the above-mentioned problems are eliminated.

A more specific object of the present invention is to provide a compact ultrasonic probe capable of forwardly emitting the ultrasonic wave.

The above-mentioned objects of the present invention are achieved by an ultrasonic probe comprising: a housing; a plurality of piezoelectric elements radially arranged in a plane substantially perpendicular to a direction in which the ultrasonic probe is inserted into a hollow portion to be scanned; and electrical means for carrying electricity to the piezoelectric elements to thereby cause the piezoelectric elements to emit ultrasonic waves and for carrying, to an external device, electric signals generated from the ultrasonic waves reflected by the hollow portion and received by the piezoelectric elements.

The above-mentioned objects of the present invention are also achieved by an ultrasonic probe comprising: a housing; a piezoelectric element provided in the housing and having a wave emitting surface contained in a plane substantially perpendicular to a direction in which the ultrasonic probe is inserted into a hollow portion; electrical means for carrying electricity to the piezoelectric element to thereby cause the piezoelectric element to emit an ultrasonic wave and for carrying, to an external device, an electric signal generated from the ultrasonic wave reflected by the hollow portion and received by the piezoelectric element; and rotating means for rotating the piezoelectric element in the plane so that the piezoelectric element moves in a circular locus in the plane.

BRIEF DESCRIPTION OF THE DRAWINGS

Other objects, features and advantages of the present invention will become more apparent from the following detailed description when read in conjunction with the accompanying drawings, in which:

FIG. 4 is a diagram illustrating the operation of the ultrasonic probe shown in FIG. 3;

DESCRIPTION OF THE PREFERRED EMBODIMENTS

Figure 1A:
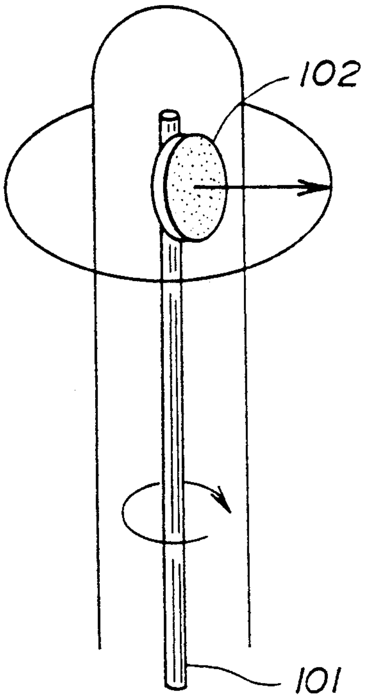
FIGS. 1A, 1B and 1C are respectively perspective views of conventional ultrasonic probes.
Figure 1B:
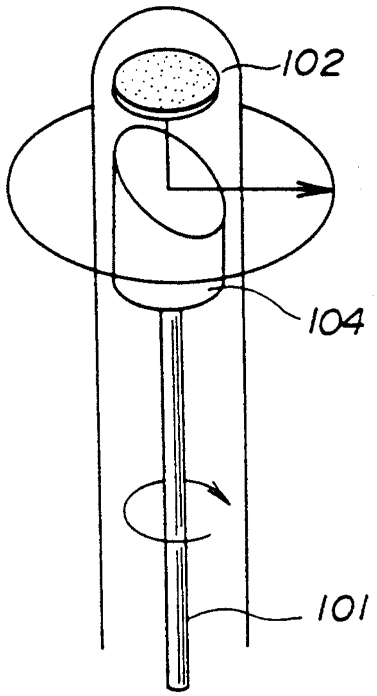
Figure 1C:
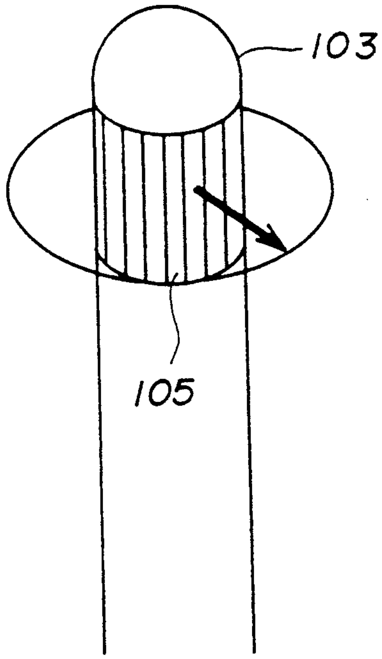
Figure 2:
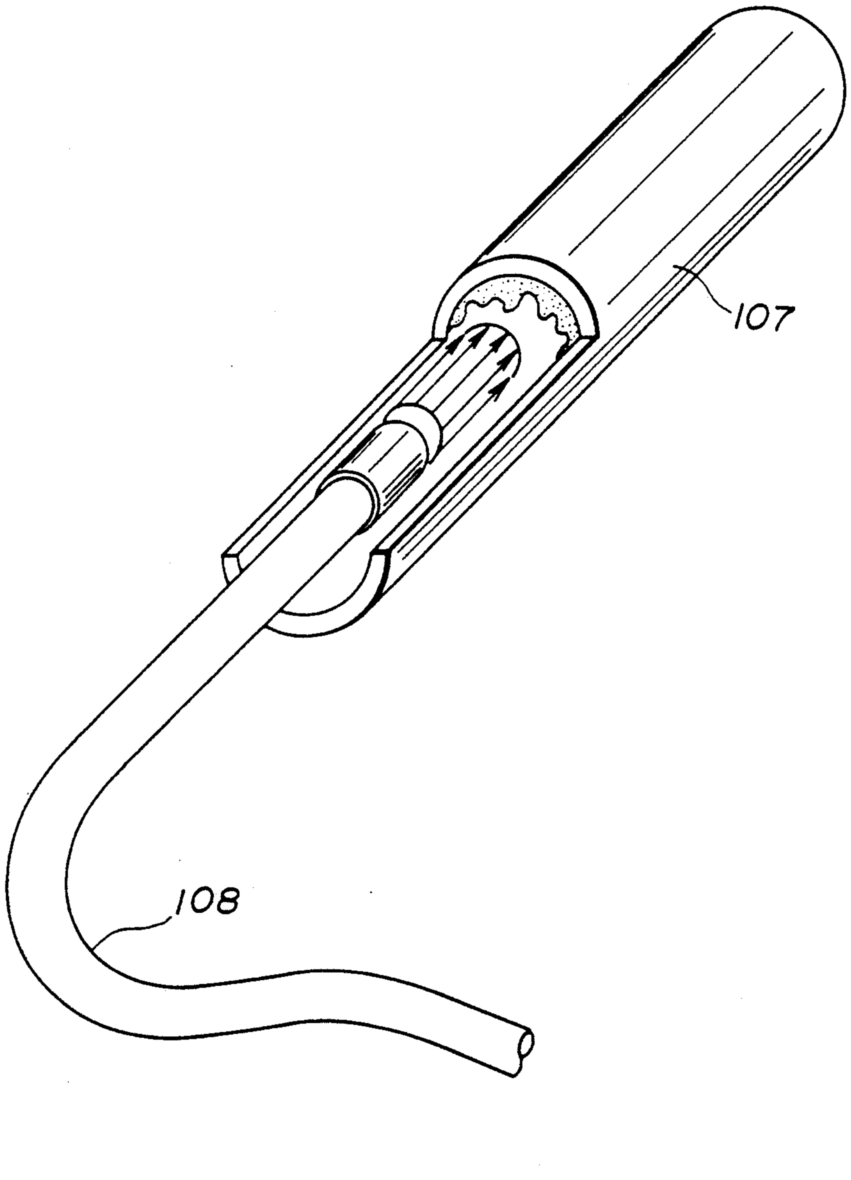
FIG. 2 is a perspective view illustrating an ultrasonic probe capable of forwardly emitting an ultrasonic wave.

A description will now be given of the principle of the ultrasonic probe according to the first preferred embodiment of the present invention with reference to FIG. 2.

Figure 3A:
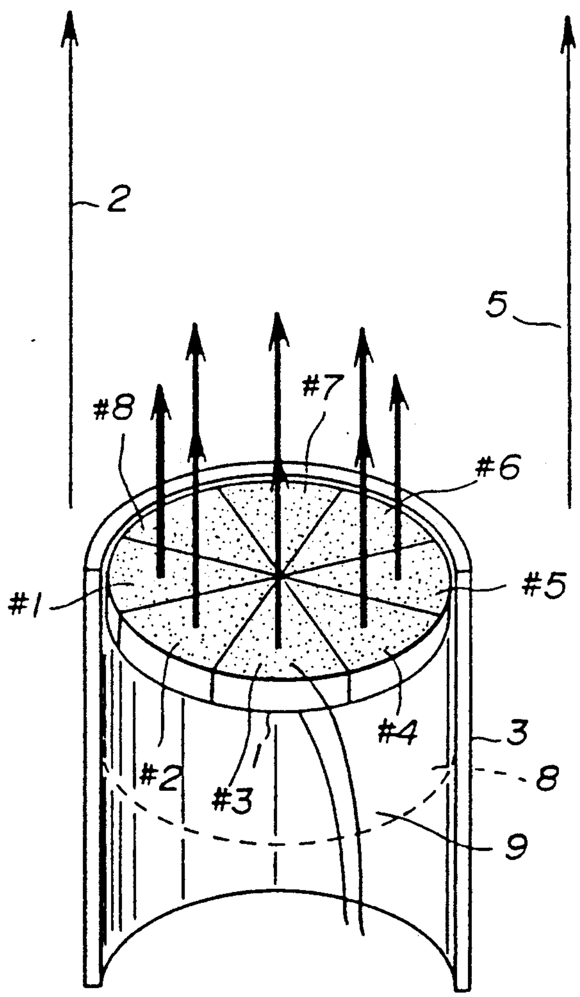
FIGS. 3*a* and 3*b* are diagram illustrating the principle of an ultrasonic probe according to a first preferred embodiment of the present invention.
Figure 3B:
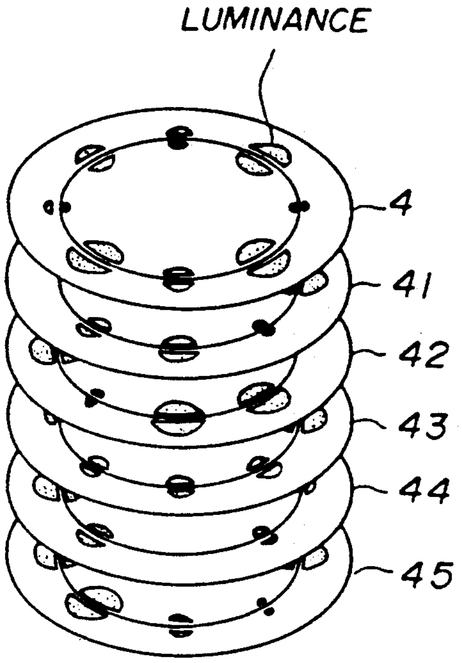

FIG. 3-(*a*) shows an ultrasonic probe 3 capable of emitting an ultrasonic wave in a direction 2 in which it is inserted into a part of a living human body, such as a blood vessel. The ultrasonic probe 3 has an assembly 1 composed of a plurality of (eight) piezoelectric elements #1–#8 arranged on a plane substantially perpendicular to the probe inserting direction 2. Each of the piezoelectric elements #1–#8 has a sectorial area, which emits an ultrasonic wave in the probe inserting direction 2 and receives a reflected ultrasonic wave. The piezoelectric elements #1–#8 can be formed by radially dividing a piezoelectric disk into eight sectorial parts starting from the center of the piezoelectric disk. Electrodes (not shown for the sake of simplicity) are formed on opposite surfaces of the disk, and lead wires 9 extend from the electrodes. The piezoelectric elements #1–#8 are held stationary in the ultrasonic probe (housing thereof) 3. For example, a backing member 8 (which will be described in detail later) fixed to an inner wall of the probe 3 is in contact with back surfaces of the piezoelectric elements #1–#8 and supports them. The ultrasonic probe 3 is inserted into a hollow tube, such as a blood vessel, and intermittently driven to emit the ultrasonic waves. The ultrasonic probe 3 receives reflection echoes from a wall of the blood vessel or a foreign substance therein. A control device (which will be described in detail later) converts the amplitude of the reflection echoes into luminance information, from which an image 4 having eight luminance information image portions (patterns) circularly located can be obtained at predetermined intervals, as shown in FIG. 3-(*b*), in which the arrow indicated by numeral 5 denotes the elapse of time. All the piezoelectric elements #1–#8 are simultaneously and intermittently driven and, as shown in FIG. 3-(*b*), a plurality of images 45, 44, 43, 42, 41 and 4 are obtained in this order as the time elapses. It will be noted that an image portion having a large size denotes a high luminance, and an image portion having a small size denotes a low luminance.

FIG. 4 is a diagram showing the operation of the ultrasonic probe 3 shown in FIG. 3. The ultrasonic probe 3 is inserted into a blood vessel 39. When sampling points 31, 32, 33, 34, 35, 36, 37 and 38 are determined, as shown in FIG. 4, images 310, 320, 330, 340, 350, 360, 370 and 380 are obtained, respectively. The images 310, 320, 330, 340, 350, 360, 370 and 380 have image portions showing luminance information shown in FIG. 4. For example, there is a foreign substance 390 deposited around the inner wall of the blood vessel 39 at the sampling point 31. Thus, all the ultrasonic waves emitted by the eight piezoelectric elements #1–#8 are reflected by the foreign substance 390 and received by the piezoelectric elements #1–#8. Thus, the corresponding image 310 has eight large luminance information image portions. The sampling points 34, 35 and 36 are located at a corner of the blood vessel 39. Thus, the corresponding images 340, 350 and 360 have respective image portions showing the corner of the blood vessel 39.

Figure 5A:
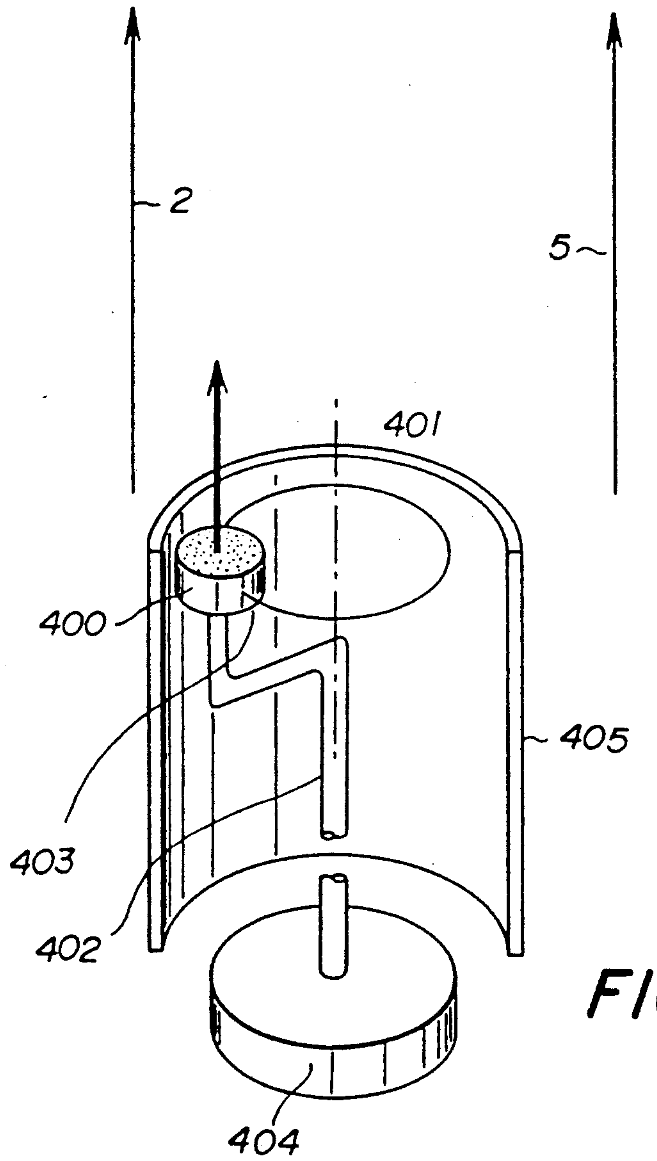
FIGS. 5*a* and 5*b* are diagram illustrating an ultrasonic probe according to a second preferred embodiment of the present invention.
Figure 5B:
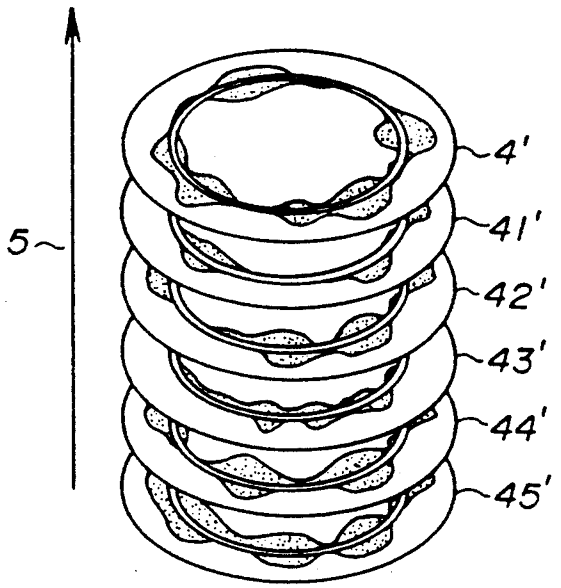

A description will now be given of the principle of an ultrasonic probe according to a second preferred embodiment of the present invention with reference to FIG. 5, in which those parts which are the same as those shown in FIG. 3 are given the same reference numerals. The ultrasonic probe has a housing 405, which accommodates a single piezoelectric element 400 in place of the aforementioned piezoelectric elements #1–#8. The piezoelectric element 400 is supported by an L-shaped shaft 402, which is rotated by a motor 404 having an axis 401. The piezoelectric element 400 is rotated along an inner surface of the probe 3 so that it has a circle locus in a plane substantially perpendicular to the axis 401 parallel to the direction 2. A wave emitting surface of the piezoelectric element 400 is substantially perpendicular to the direction of the axis 401. Lead wires, which are electrically connected to respective electrodes formed on opposite surfaces of the piezoelectric element 400, extend along the shaft 402, and are connected to the control device (now shown). By intermittently driving the piezoelectric element 400 while it is rotating, images 45', 44', 43', 42', 41' and 4' having substantially continuous image portions located on a circle and showing luminance information are obtained in this order. Such continuous image portions will have precise positional information indicating the inner wall of the blood vessel wall or a foreign substrate deposited thereon, as compared with the image portions shown in FIG. 3.

Figure 6A:
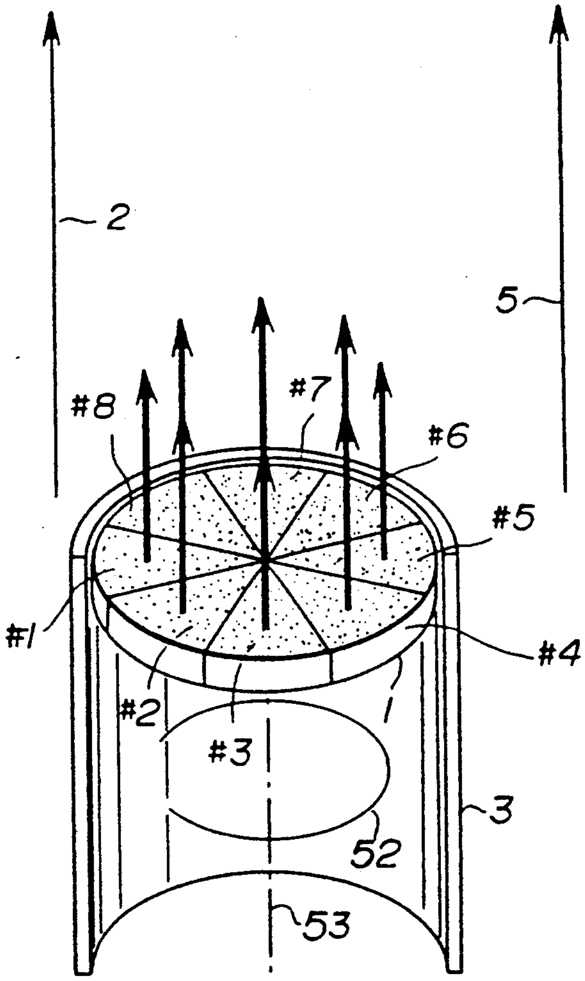
FIGS. 6*a* and 6*b* are a diagram illustrating an ultrasonic probe according to a third preferred embodiment of the present invention.
Figure 6B:
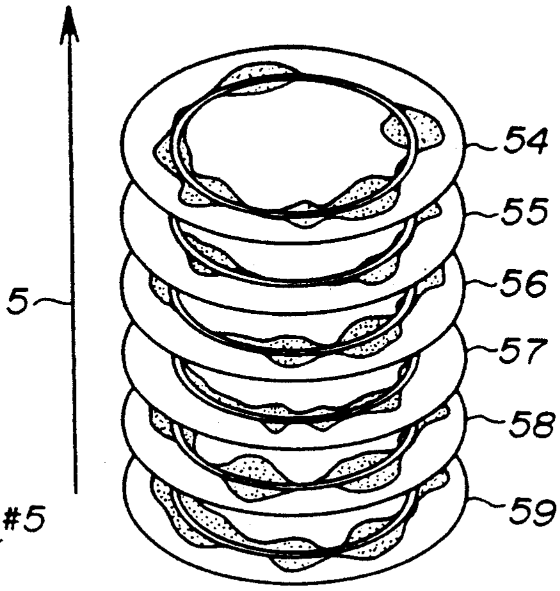
Figure 7A:
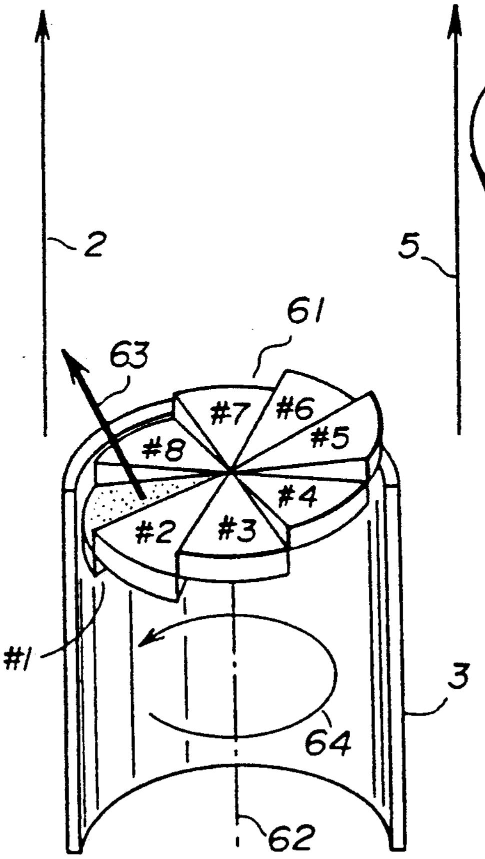
FIGS. 7*a* and 7*b* and 7*c* and 7*d* a diagram illustrating the principle of an ultrasonic probe according to a fourth preferred embodiment of invention.
Figure 7B:
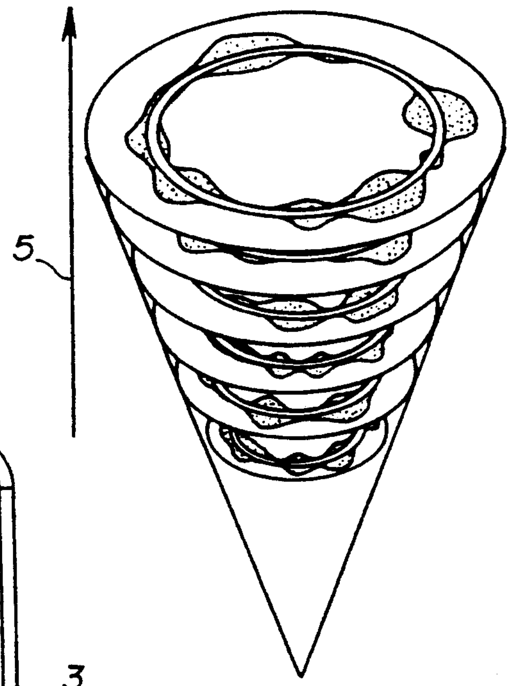
Figure 7C:
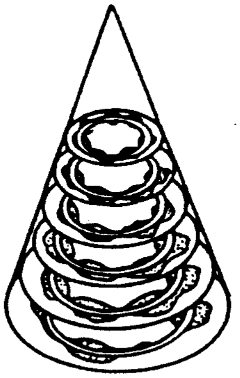
Figure 7D:
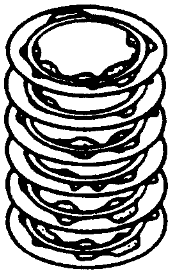

FIG. 6 illustrates a third preferred embodiment of the present invention. The assembly 1 of the piezoelectric elements #1–#8, which are the same as those shown in FIG. 3, is rotatably provided in the ultrasonic probe 3. It will be noted that the 20 piezoelectric elements #1–#8 of the first preferred embodiment of the present invention are held stationary. The piezoelectric elements #1–#8 are driven to emit the ultrasonic waves while they are integrally rotating around the axis 53, as indicated by a line 52 shown in FIG. 6. Thereby, images 59, 58, 57, 56, 55 and 54 having substantially continuous luminance information image portions circularly formed are obtained in this order. It should be noted that each of the images 54–59 can be obtained by one-eighth of a revolution of the assembly of the piezoelectric element assembly 1. On the other hand, according to the first embodiment of the present invention, the same scanning area is covered when one revolution of the assembly 1 of the piezoelectric elements #1–#8 is completed.

FIG. 7 is a diagram illustrating a fourth preferred embodiment of the present invention. An assembly 61 including eight substantially sectorial piezoelectric elements #1–#8 is provided so that it rotates around a rotating axis 62. Each of the piezoelectric elements #1–#8 has an inclined wave emitting surface. It is preferable that the degrees of slops of the inclined wave emitting surfaces of the piezoelectric elements #1 through #8 with respect to the direction perpendicular to the axis 62 be different from each other. For example, the ultrasonic wave emitted from the piezoelectric element #1 goes outwardly, and the ultrasonic wave emitted from the piezoelectric element #5 goes inwardly. The ultrasonic emitting surface of the piezoelectric element #3 is perpendicular to the rotating axis 62, so that the ultrasonic wave emitted therefrom goes in the direction in which the rotating axis 62 extends.

When the piezoelectric element #1 is selected, as shown in FIG. 7-(*b*), luminance information images which conically expand in the probe inserting direction 5 are obtained. When the piezoelectric element #5 is selected, as shown in FIG. 7-(*c*), luminance information images which conically converge in the probe inserting direction 5 are obtained. When the piezoelectric element #3 is selected, luminance information images of almost the same size are obtained. With the ultrasonic probe 3 shown in FIG. 7-(*a*), it becomes possible to obtain various visual fields in front of the ultrasonic wave 3.

Figure 8A:
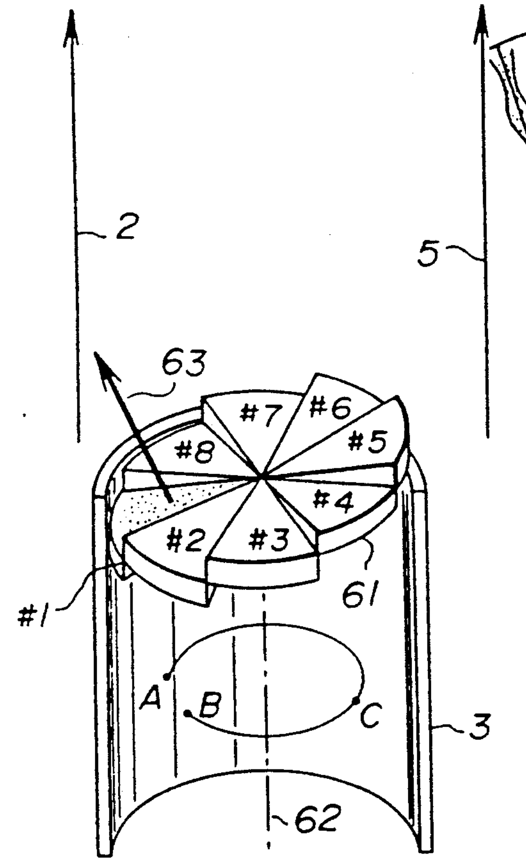
FIGS. 8*a* and 8*b* and 8*c* are a of an ultrasonic probe according to a fifth preferred embodiment of the present invention.
Figure 8B:
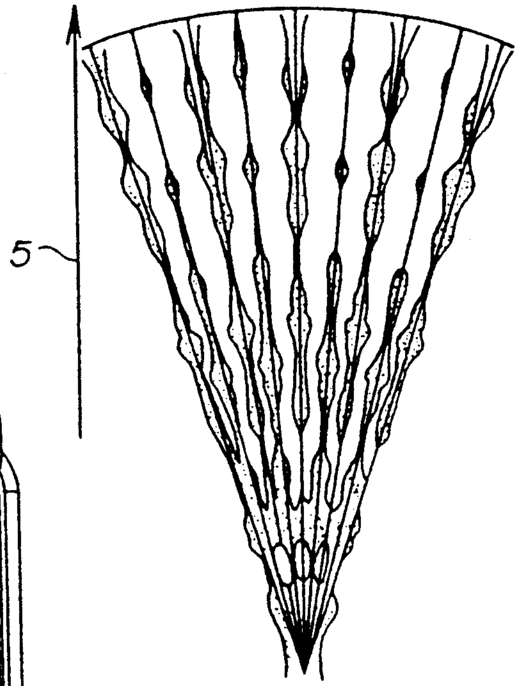
Figure 8C:
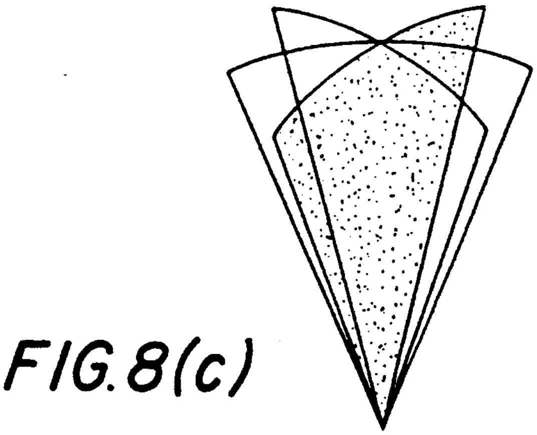
Figure 9:
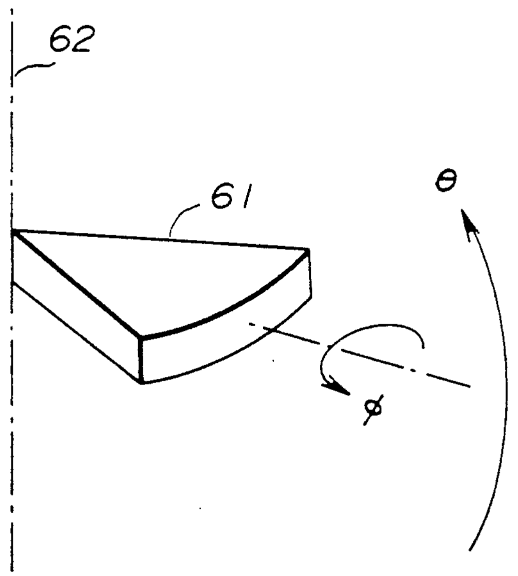
FIG. 9 is a diagram illustrating incline each piezoelectric element is inclined.

A description will now be given of the principle of an ultrasonic probe according to a fifth preferred embodiment of the present invention with reference to FIG. 8. The ultrasonic probe 3 shown in FIG. 8-(*a*) also uses the assembly 61 of piezoelectric elements shown in FIG. 7-(*a*). However, the procedure for driving the piezoelectric element assembly 61 shown in FIG. 8-(*a*) is different from that of the assembly 61 shown in FIG. 7-(*a*). Each of the piezoelectric elements #1–#8 which are rotating is driven at a position A, and the reflected wave is received at almost the same position. It will be noted that the propagation speed of the ultrasonic wave is much faster than the rotating speed of the assembly 61. FIG. 8-(*a*) shows that the piezoelectric element #1 is located at the position A and is driven. Next, the piezoelectric element #2 will be driven at the position A when it is rotating in the clockwise direction. The above-mentioned driving procedure provides a two-dimensional sector-shaped luminance information image, as shown in FIG. 8-(*b*). Further, by changing the driving and receiving position from A to B or C shown in FIG. 8-(*a*), sector-shaped luminance information images having different directions are obtained, as shown in FIG. 8-(*c*). If the driving and receiving position is sequentially changed, a three-dimensional luminance information image can be obtained.

It is possible to incline the piezoelectric elements #1–#8 shown in FIG. 7-(*a*) or FIG. 8-(*a*) in a direction $\theta$ or direction $\phi$.

Figure 10A:
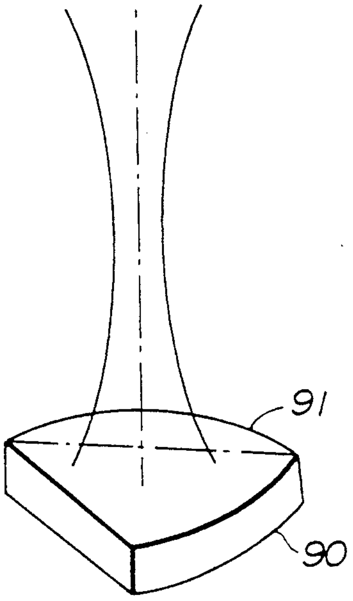
FIGS. 10A and 10B are respectively diagrams illustrating variations of the piezoelectric element used in the present invention.

In each of the above-mentioned embodiments of the present invention, as shown in FIG. 10A, it is possible to provide an acoustic lens 91 for converging the ultrasonic wave on the ultrasonic wave emitting surface of each element. The ultrasonic wave is focused at the focal point of the acoustic lens 91, so that an improved resolution of an area in the vicinity of the focal point can be obtained.

Figure 10B:
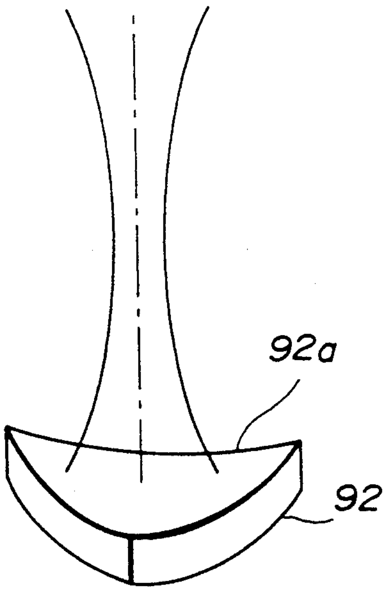
Figure 10A:
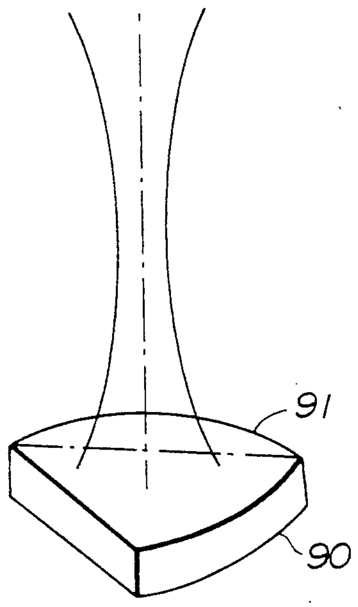
Figure 10B:
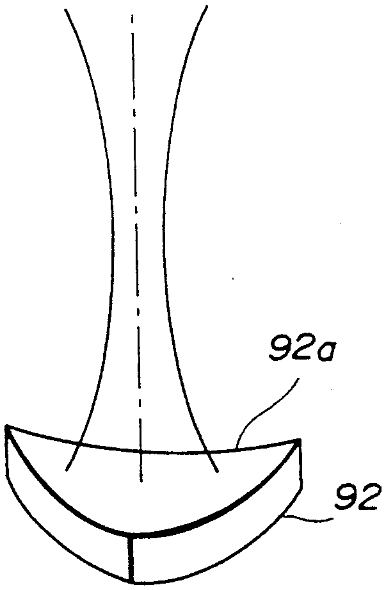

FIG. 10B shows a variation 92 of the piezoelectric element. The variation 92 shown in FIG. 10B has a concave ultrasonic wave emitting surface 92*a*. The ultrasonic wave emitted from the concave wave emitting surface 92*a* is focused at the focal point thereof, so that an improved resolution of an area in the vicinity of the focal point can be obtained.

Figure 11:
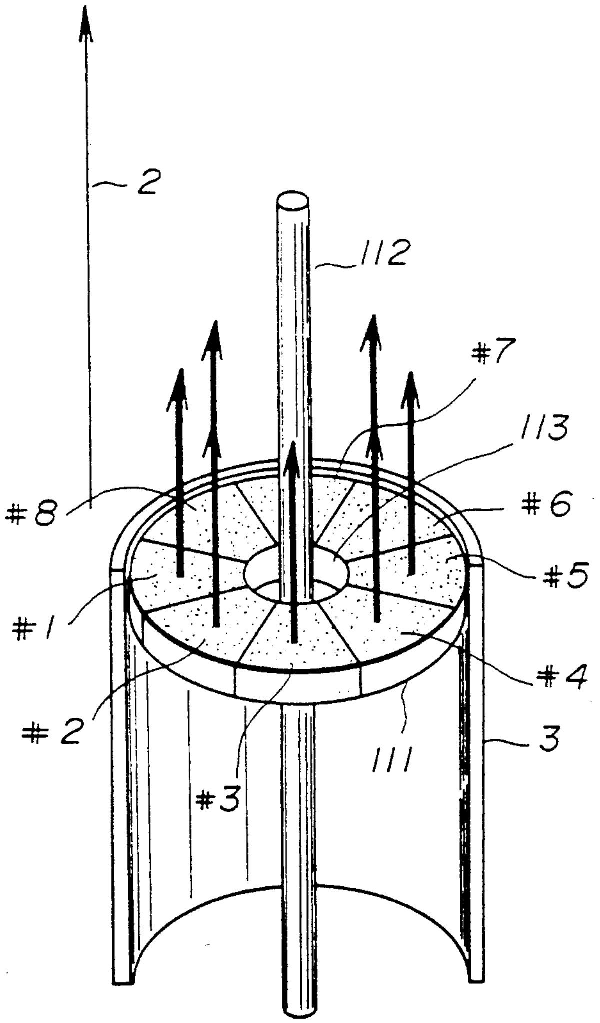
FIG. 11 is a perspective view illustrating a variation of the embodiments of the present invention.

FIG. 11 shows a variation of the piezoelectric element assemblies used in the aforementioned first, third, fourth and fifth embodiments of the present invention. For the sake of simplicity, only a variation of the first embodiment is illustrated in FIG. 11. The ultrasonic probe 3 has a ring-shaped piezoelectric assembly 111 having a plurality of sector-shaped piezoelectric elements #1–#8. An instrument 112 penetrates a through hole 113 formed at the center of the assembly 111. The instrument 112 is, for example, a cutter for removing a foreign substance in a blood vessel, a laser beam fiber, a medical substance injecting tube, a guide which guides the ultrasonic probe 3 or the like.

Figure 12A:
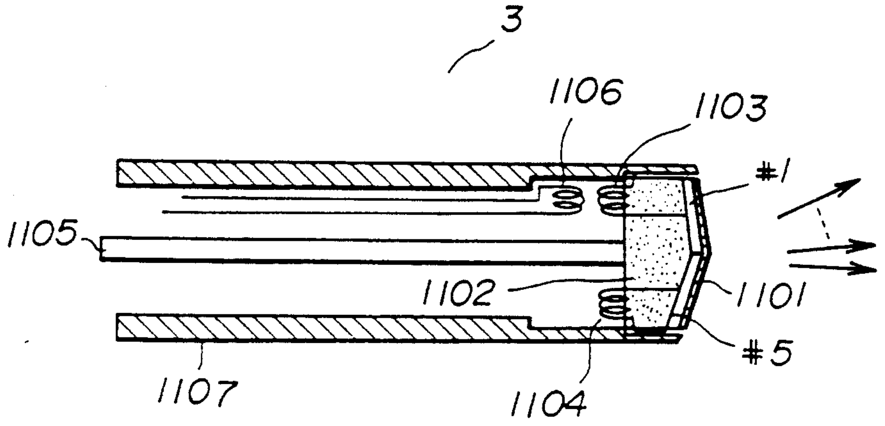
FIGS. 12A and 12B are respectively cross-sectional view of a front portion of the ultrasonic probe according to the present invention.
Figure 12B:
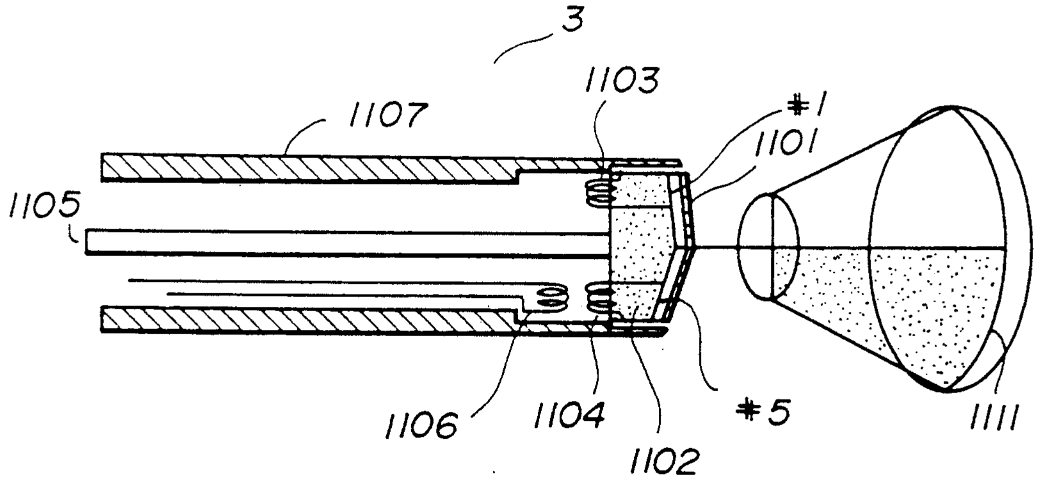

The structure of the ultrasonic probe 3 according to the present invention will now be described more specifically, with reference to FIGS. 12A and 12B, which respectively illustrate a front portion of the ultrasonic probe. The ultrasonic probe 3 has a housing 1107, in which a piezoelectric element assembly, such as the piezoelectric assembly 61 shown in FIG. 7 or FIG. 8, is provided. In FIGS. 12A and 12B, two piezoelectric elements #1 and #5 are illustrated. The piezoelectric elements used in the structure shown in FIGS. 12A and 12B are inclined so that the ultrasonic waves emitted therefrom go outwardly. An impedance matching layer 1101 is provided on the entire ultrasonic wave emitting surface of the piezoelectric element assembly 61. When the aforementioned acoustic lens 91 is used, the impedance matching layer 1101 is provided on the acoustic lens 91. The impedance matching layer 1101 makes an impedance matching with an area in which the emitted wave penetrates, and is formed of, for example, an epoxy resin containing metallic particles. A backing member 1102 is formed on a back surface of the piezoelectric element assembly 61 opposite to the ultrasonic wave emitting surface. The backing member 1102 absorbs unnecessary vibrations and functions as a damper. The backing member 1102 is formed of, for example, an epoxy resin containing metallic particles.

Coils are provided for the respective piezoelectric elements #1–#8 (only coils 1103 and 1104 related to the piezoelectric elements #1 and #5 are illustrated). Each of the coils is connected to the electrodes of a corresponding one of the piezoelectric elements #1–#8 via driving lead wires. The piezoelectric element assembly 61, the matching layer 1101 and the backing member 1103 are connected to a rotating shaft 1105. A stationary coil 1106 is provided in the housing 1107. By passing a current through the stationary coil 1106, the piezoelectric elements #1–#8 are driven in turn due to the electromagnetic coupling. Thus, while the piezoelectric element assembly 61 is rotating, electrical energy can be supplied to the piezoelectric elements #1–#8 in turn. The position of the stationary coil 1106 determines the scanning area, as shown in FIG. 12B. If the stationary coil 1106 is positioned as shown in FIG. 12B, an area 1111 in front of the ultrasonic probe 3 can be scanned.

Figure 13A:
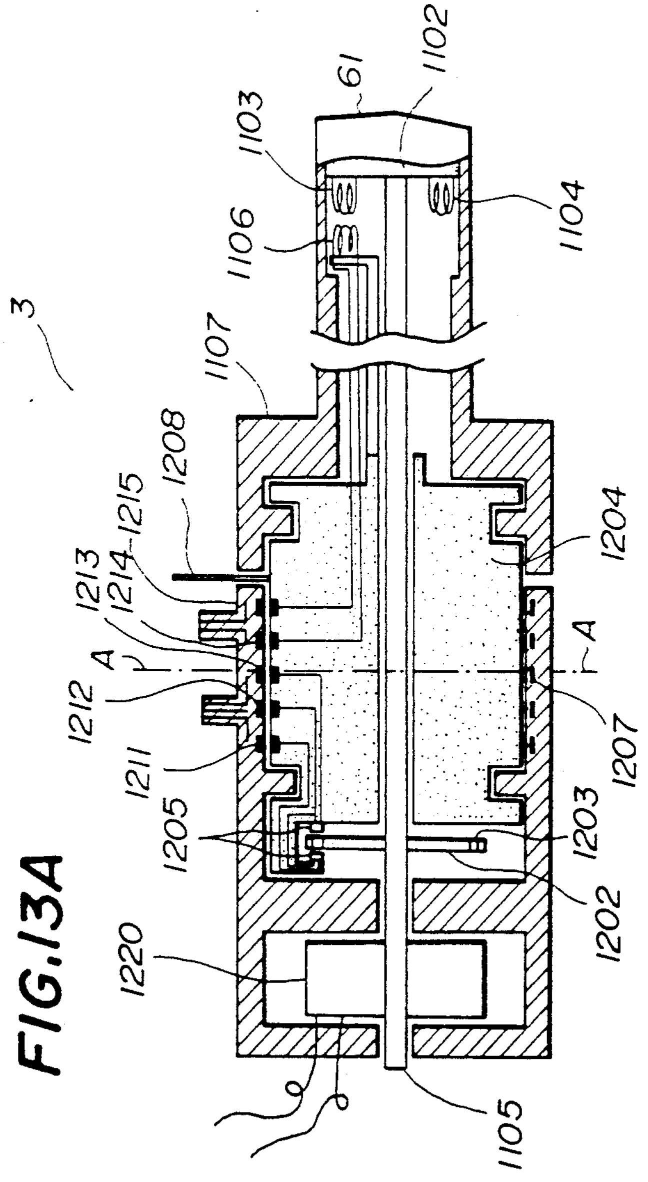
FIGS. 13A and 13B are cross-sectional views showing a rear portion of the ultrasonic probe according to the present invention.

FIG. 13A shows a rear portion of the ultrasonic probe together with the front portion thereof. The housing 1107 has a rear portion having a diameter greater than the front portion. A motor 1220, which is provided in a back end portion of the housing 1107, rotates the rotating shaft 1105. A disk 1202 connected to the rotating shaft 1105 is provided for detecting the rotating position of the rotating shaft 1105. A plurality of holes 1202 are provided in the disk 1202. The positions of the holes 1203 correspond to the coils including the coils 1103 and 1104, and correspond to the coils provided for the respective piezoelectric elements #1–#8. A rotating block 1204 is provided in the housing 1107. The rotating shaft 1105 penetrates the rotating block 1204 in its axial direction. The rotating block 1204 is rotatable separately from the rotating shaft 1105. A photosensor 1205 composed of a light emitting element and a photoconductive element is fixed to the rotating block 1204 so that a light emitted from the light emitting element passes through the hole 1205 and is received by the photoconductive element. The photosensor 1205 is connected, through wiring leads passing inside the rotating block 1204. to terminals 1211, 1212 and 1213 formed on a circumferential surface of the rotating block 1204.

Figure 13B:
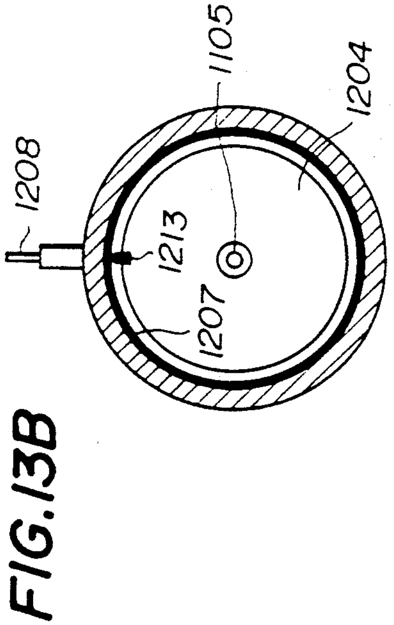

FIG. 13B is a cross-sectional view taken along line A—A shown in FIG. 13A. A ring-shaped terminal 1207, which is in contact with the terminal 1213, is formed on an inner wall of the housing 1107. A lever 1208 is fixed to the rotating block 1204. A ring-shaped groove is provided in the housing 1107 so that it projects therefrom. By turning the lever 1208 in the clockwise or counterclockwise direction, the rotating block 1204 is rotated. Since the stationary coil 1106 is fixed to the rotating block 1204, it is possible to change the position of the stationary coil 1106 by turning the lever 1208. The stationary coil 1106 is electrically connected to terminals 1214 and 1215 formed on the circumferential surface of the rotating block 1204. Two ring-shaped electrodes are provided in the inner wall of the housing 1107 so that they are opposite to the terminals 1214 and 1215, respectively. Although not shown for the sake of simplicity, external leads are connected to the electrodes provided on the inner wall of the housing 1107.

The piezoelectric element assembly 61 is rotated by the motor 1220. During this operation, the disk 1202 is also rotated. When the light emitted from the light emitting element of the photosensor 1205 is received by the photoconductive element through the hole 1203 formed in the disk 1202, a pulse signal is generated by the photoconductive element and output via two corresponding terminals out of the terminals 1211, 1212 and 1213. It will be noted that each time such a pulse signal is output, the stationary coil 1103 faces one of the eight coils, including the coils 1103 and 1104. Each time this happens, electricity is supplied to the stationary coil 1106 via the terminals 1214 and 1215 and corresponding terminals formed on the inner wall of the housing 1107. Then, an electromagnetic inducement occurs between the stationary coil and the opposite rotating coil. Thus, the corresponding piezoelectric element is driven, so that an ultrasonic wave is emitted therefrom. By changing the position of the stationary coil 1106 by the lever 1208, it is possible to change the scanning area, as has been described previously.

Figure 14:
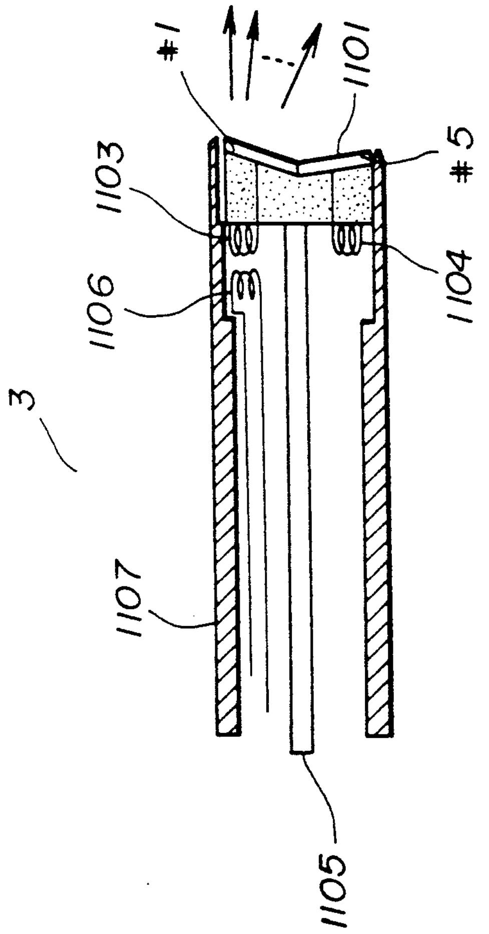
FIG. 14 is a cross-sectional view of a variation of the structure shown in FIGS. 12A and 12B.

FIG. 14 shows a variation of the front portion of the ultrasonic probe shown in FIGS. 13A and 13B. The cross section of the piezoelectric assembly has a concave shape so that the ultrasonic wave goes inwardly.

The piezoelectric elements mentioned above are formed of, for example, PZT, and each has a diameter equal to, for example, 1.5 mm.

Figure 15:
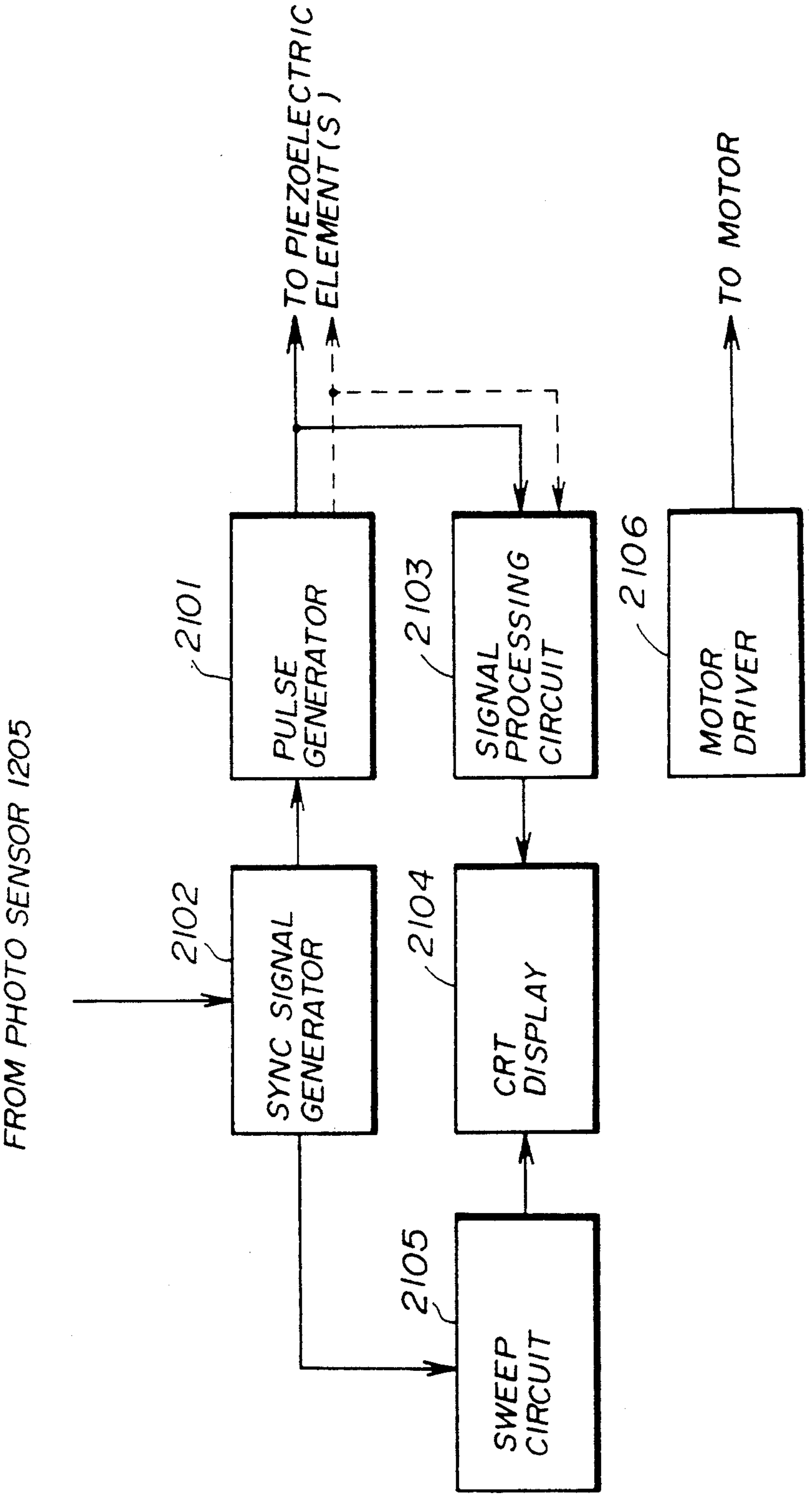
FIG. 15 is a block diagram of a control device for controlling the ultrasonic probe according to the present invention.

FIG. 15 illustrates a control device coupled to the ultrasonic probe according to the present invention. The control device shown in FIG. 14 is made up of a pulse generator 2101, a synchronizing signal generator 2102, a signal processing circuit 2103, a CRT display device 2104, a sweep circuit 2105 and a motor driver 2106. The synchronizing signal generator 2102 generates a synchronizing signal by referring to a signal from the photosensor 1205, and supplies it to the pulse generator 2101 and the sweep circuit 2105. The pulse generator 2101 generates a pulse signal or pulse signals in response to the synchronizing signal. For example, the pulse generator 2101 intermittently generates a series of pulses, each having a voltage equal to, for example, 100 volts and a pulse duration of time equal to, for example, 0.05 microseconds. In the second embodiment, such pulses are applied to all the piezoelectric elements #1–#8 at the same time. The signal processing circuit 2103 receives the reflected ultrasonic waves and generates a video signal therefrom in a conventional manner. For example, the reflected ultrasonic wave has a time duration between 1 and 2 microseconds. The sweep circuit 2105 generates a sweep signal in response to the synchronizing signal from the synchronizing signal generator 2102, and outputs the sweep signal to the CRT display device 2104. The CRT display device 2104 shows an image generated by the video signal in accordance with the sweep signal. The motor driver 2106 generates a driving signal applied to the aforementioned motor.

The present invention is not limited to the specifically disclosed embodiments, and variations and modifications may be made without departing from the scope of the present invention.

What is claimed is:

1. An ultrasonic probe for insertion into a part of a patient body, comprising:

a housing;

a plurality of piezoelectric elements radially disposed in said housing in a plane substantially perpendicular to a direction in which the ultrasonic probe is inserted into said part of said patient body, said plurality of piezoelectric elements facing toward a distal end of said housing, directing an ultrasonic wave in said direction in which said probe is inserted; and electrical means for carrying electricity to said piezoelectric elements to thereby cause said piezoelectric elements to emit ultrasonic waves and for carrying, to an external device, electric signals generated from said ultrasonic waves reflected by said patient body and received by said piezoelectric elements.

2. An ultrasonic probe as claimed in claim 1 wherein said piezoelectric elements are firmly secured in said housing.

3. An ultrasonic probe as claimed in claim 1, wherein said ultrasonic probe further comprises:

a shaft provided in said housing and supporting said piezoelectric elements; and rotating means for rotating said shaft so that said piezoelectric elements are integrally rotated.

4. An ultrasonic probe as claimed in claim 1, wherein:

each of said piezoelectric elements has a substantially identical sectorial surface;

said piezoelectric elements are arranged side by side so that an assembly of said piezoelectric elements has a disc shape.

5. An ultrasonic probe as claimed in claim 1, wherein said plurality of said piezoelectric elements has a through hole.

6. An ultrasonic probe as claimed in claim 1, wherein said piezoelectric elements have wave emitting surfaces which are located in said plane.

7. An ultrasonic probe as claimed in claim 1, wherein said piezoelectric elements have wave emitting surfaces which are inclined with respect to said plane.

8. An ultrasonic probe as claimed in claim 7, wherein said wave emitting surfaces of said piezoelectric elements are inclined with respect to said plane at different angles.

9. An ultrasonic probe as claimed in claim 7. wherein said wave emitting surfaces of said piezoelectric elements include a wave emitting surface from which an ultrasonic wave is outwardly emitted so that the ultrasonic wave goes away from an axis of said ultrasonic probe substantially corresponding to said direction.

10. An ultrasonic probe as claimed in claim 7, wherein said wave emitting surfaces of said piezoelectric elements include a wave emitting surface from which an ultrasonic wave is inwardly emitted so that said ultrasonic wave goes toward an axis of the ultrasonic probe substantially corresponding to said direction.

11. An ultrasonic probe for insertion into a part of a patient body, comprising:

a housing;

a plurality of piezoelectric elements radially disposed in said housing in a plane substantially perpendicular to a direction in which the ultrasonic probe is inserted into said part of said patient body;

electrical means for carrying electricity to said piezoelectric elements to thereby cause said piezoelectric elements to emit ultrasonic waves and for carrying, to an external device, electrical signals generated from said ultrasonic waves reflected by said patient body and received by said piezoelectric elements; and acoustic lenses respectively provided on said piezoelectric elements, said acoustic lenses focusing ultrasonic waves emitted from said piezoelectric elements.

12. An ultrasonic probe for insertion into a part of a patient body, comprising:

a housing;

a plurality of piezoelectric elements radially disposed in said housing in a plane substantially perpendicular to a direction in which the ultrasonic probe is inserted into said part of said patient body;

electrical means for carrying electricity to said piezoelectric elements to thereby cause said piezoelectric elements to emit ultrasonic waves and for carrying, to an external device, electrical signals generated from said ultrasonic waves reflected by said patient body and received by said piezoelectric elements; and wherein said piezoelectric elements include concave wave emitting surfaces which cause ultrasonic waves emitted therefrom to be focused.

13. An ultrasonic probe for insertion into a part of a patient body, comprising:

a housing;

a plurality of piezoelectric elements radially disposed in said housing in a plane substantially perpendicular to a direction in which the ultrasonic probe is inserted into said part of said patient body;

electrical means for carrying electricity to said piezoelectric elements to thereby cause said piezoelectric elements to emit ultrasonic waves and for carrying, to an external device, electrical signals generated from said ultrasonic waves reflected by said patient body and received by said piezoelectric elements;

a shaft provided in said housing and supporting said piezoelectric elements; and rotating means for rotating said shaft so that said piezoelectric elements are integrally rotated;

wherein said electrical means comprises:

first coils respectively connected to said piezoelectric elements and rotating together with said piezoelectric elements; and a second coil located so that said second coil faces said first coils while said piezoelectric elements are being rotated by said rotating means, wherein said electricity is supplied to said second coil, and said piezoelectric elements receive said electricity from said second coil through said first coils, so that said piezoelectric elements are driven to emit the ultrasonic waves.

14. An ultrasonic probe as claimed in claim 13, wherein said ultrasonic probe comprises means for changing a position of said second coil.

15. An ultrasonic probe as claimed in claim 13, wherein said ultrasonic probe further comprises position detecting means for detecting positions of said piezoelectric elements which are being rotated by said rotating means.

16. An ultrasonic probe as claimed in claim 15, wherein said position detecting means comprises:

a disk member fixed to said shaft and having at least one hole therein; and a photosensor having a light emitting element and a photoconductive element, wherein a light emitted from said light emitting element passes through said one hole and is received by said photoconductive element; and said photosensor is located at a position corresponding to the position of said second coil.

17. An ultrasonic probe as claimed in claim 16, wherein:

said ultrasonic probe comprises a rotating block which is rotatably supported in said housing separately from said piezoelectric elements; and said second coil and said photosensor are fixed to said rotating block.

18. An ultrasonic probe as claimed in claim 17, wherein:

said rotating block has a substantially cylindrical shape and said housing has a cylindrical hollow portion has a shape which substantially corresponds to said cylindrical shape of said rotating block, said rotating block being disposed within said cylindrical hollow portion, and wherein said ultrasonic probe comprises:

a first group of electrodes connected to said second coil and provided on a circumferential surface of said rotating block;

a second group of electrodes connected to said photosensor and provided on said circumferential surface of said rotating block; and a third group of ring-shaped electrodes provided on an inner surface of said housing defining said cylindrical hollow portion and positioned so that said third group of ring-shaped electrodes are in contact with said first and second groups of electrodes.

19. An ultrasonic probe as claimed in claim 18, wherein said ultrasonic probe comprises a lever fixed to said rotating block, so that said rotating block is positioned by turning said lever.

20. An ultrasonic probe for insertion into a part of a patient body, comprising:

a housing;

a plurality of piezoelectric elements radially disposed in said housing in a plane substantially perpendicular to a direction in which the ultrasonic probe is inserted into said part of said patient body;

electrical means for carrying electricity to said piezoelectric elements to thereby cause said piezoelectric elements to emit ultrasonic waves and for carrying, to an external device, electrical signals generated from said ultrasonic waves reflected by said patient body and received by said piezoelectric elements;

a shaft provided in said housing and supporting said piezoelectric elements; and rotating means for rotating said shaft so that said piezoelectric elements are integrally rotated;

wherein said ultrasonic probe further comprises an acoustic impedance matching layer provided on said piezoelectric elements.

21. An ultrasonic probe for insertion into a part of a patient body, comprising:

a housing;

a piezoelectric element disposed in said housing, and having a wave emitting surface contained in a plane substantially perpendicular to a direction in which said ultrasonic probe is inserted into said patient body, said wave emitting surface facing toward a distal end of said housing, directing an ultrasonic wave in said direction in which said probe is inserted;

electrical means for carrying electricity to said piezoelectric elements to thereby cause said piezoelectric element to emit said ultrasonic wave and for carrying, to an external device, an electrical signal generated from said ultrasonic wave reflected by said patient body and received by said piezoelectric element; and rotating means for rotating said piezoelectric element in said plane so that said piezoelectric element moves in a circular locus in said plane.

22. An ultrasonic probe as claimed in claim 21, wherein said wave emitting surface of said piezoelectric element has a concave portion which functions to focus said ultrasonic wave.

23. An ultrasonic probe as claimed in claim 21, wherein said ultrasonic probe comprises an acoustic lens which is provided on said wave emitting surface and which functions to focus said ultrasonic wave.

24. An ultrasonic probe as claimed in claim 21, wherein said piezoelectric element has a disk shape.

* * * * *